United States Patent

Hughes et al.

[11] 3,994,891
[45] Nov. 30, 1976

[54] TETRAHYDROISOQUINOLINE COMPOUNDS

[75] Inventors: John Lawrence Hughes, Kankakee; Jay Kenneth Seyler, Bourbonnais, both of Ill.

[73] Assignee: Armour Pharmaceutical Company, Phoenix, Ariz.

[22] Filed: Dec. 20, 1974

[21] Appl. No.: 534,742

[52] U.S. Cl. .................. 260/247.5 GP; 260/246 B; 260/268 TR; 260/268 BQ; 260/288 A; 260/288 CF; 260/288 CE; 424/248; 424/250; 424/258
[51] Int. Cl.² .................................... C07D 413/06
[58] Field of Search ........... 260/247.5 GP, 268 BQ, 260/288 A, 288 CE, 288 CF, 246 B, 288 D

[56] References Cited
UNITED STATES PATENTS

| | | | |
|---|---|---|---|
| 3,362,956 | 1/1968 | Archer | 260/268 BQ |
| 3,846,432 | 11/1974 | Tanaka et al | 260/288 D |

*Primary Examiner*—Henry R. Jiles
*Assistant Examiner*—R. W. Ramsuer
*Attorney, Agent, or Firm*—Richard R. Mybeck; Carl C. Batz

[57] ABSTRACT

Tetrahydroisoquinoline compounds represented by the formula:

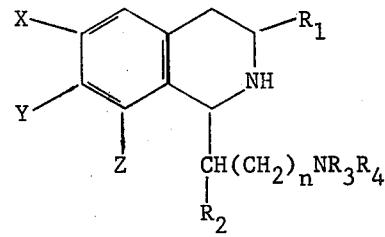

in which
  X is a hydroxy group,
  Y is a hydroxy group or
  Y taken with X is —O—CH$_2$—O—,
  Z is hydrogen or a hydroxy group,
  R$_1$ is hydrogen or an alkyl group of one to four carbon atoms,
  R$_2$ is hydrogen, an alkyl group of one to four carbon atoms or phenyl, pyrrolidinomethyl, piperidinomethyl, or morpholinomethyl,
  R$_3$ and R$_4$ each is an alkyl group of one to four carbon atoms or R$_3$ taken with R$_4$ and N is pyrrolidinyl, piperidino, morpholino, or 2-(1,2,3,4-tetrahydroisoquinolyl), and
  $n$ is one or zero, which compounds are effective as vasodilators, processes for the preparation of these compounds, and intermediate compounds useful in the preparation of such compounds.

13 Claims, No Drawings

TETRAHYDROISOQUINOLINE COMPOUNDS

This invention relates to certain tetrahydroisoquinoline compounds, to intermediates useful in the preparation of such compounds and to processes for the preparation of such compounds and intermediates. Such tetrahydroisoquinoline compounds are useful in the treatment of vasospastic conditions and peripheral vascular disease.

BACKGROUND OF THE INVENTION

A common disease, especially among elderly human patients, involves the resistance of blood vessels to the flow of blood resulting in a lowering of the amount of oxygen delivered to muscles and skin at extremities of the body such as the hands or feet and giving rise, for example, to the sensation of cold feet and intermittent claudication.

Several drugs are known which when administered to patients suffering from such vascular diseases will increase blood flow by decreasing the resistance of the blood vessels. Some of these known drugs have unwanted side effects which makes them less desirable than others.

Among the known drugs which are capable of reducing resistance to blood flow, called peripheral vasodilators, are nicotinic acid, which has the formula:

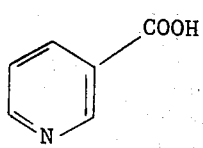

nicotinyl alcohol which has the formula:

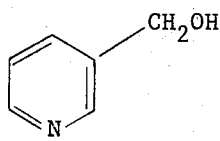

isoxsuprine which has the formula:

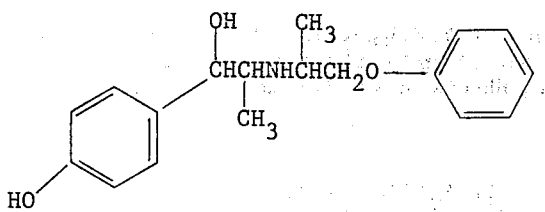

tolazoline which has the formula:

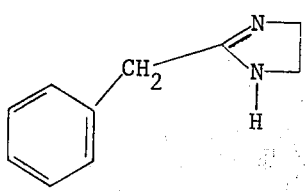

nylidrin, papaverine and cyclandelate. Of the above-named drugs, nylidrin and isoxsuprine have perhaps been more commonly administered for the relief of peripheral vascular diseases. But the search continues for vasodilator drugs which are more effective in reducing blood vessel resistance or which may have fewer side effects. Many patients who suffer from the effects of restriction to blood flow also have heart disease of some kind, and treatment with some of the known vasodilators, which also have an effect on the heart, may be too hazardous. Unwanted cardiovascular effects which have been recorded include hypertension, tachycardia, palpitations and postural hypotension. Other side effects may include headache, nausea, dizziness, nasal congestion, flushing and tingling sensations.

DESCRIPTION OF THE INVENTION

We have discovered a group of vasodilator drugs which are found to be effective for reducing the blood vessel resistance to flow of blood and which, at the same time, are relatively free of unwanted side effects. These compounds are tetrahydroisoquinoline compounds represented by the formula:

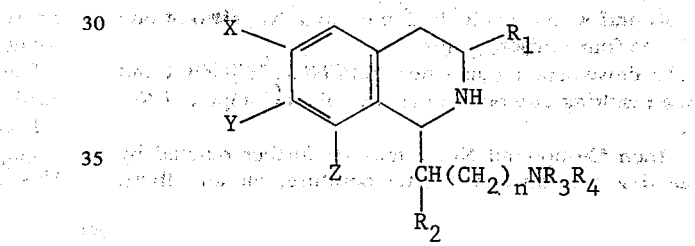

General Formula wherein

X is a hydroxy group and

Y is a hydroxy group, or

X taken with Y is a methylenedioxy group (—O—CH$_2$—O—)

Z is hydrogen or a hydroxy group, $R_1$ is hydrogen or an alkyl group of one to four carbon atoms, $R_2$ is hydrogen, an alkyl group of one to four carbon atoms, phenyl, pyrrolidinomethyl, piperidinomethyl, morpholinomethyl, $R_3$ and $R_4$ each is an alkyl group of one to four carbon atoms or $R_3$ taken with $R_4$ and N is pyrrolidinyl, piperidino, morpholino, 1-(4-alkylpiperazinyl) where alkyl has one to four carbon atoms, or 2-(1,2,3,4-tetrahydroisoquinolyl), and n is one or zero and the pharmaceutically acceptable acid addition salts of said compounds.

To prepare the compounds above defined we may start by the addition of an acryloyl chloride to a solution of a phenethylamine in an inert solvent such as benzene at a temperature of about 0 to 10° C, followed by the addition of an aqueous sodium hydroxide solution. This reaction may be written as follows:

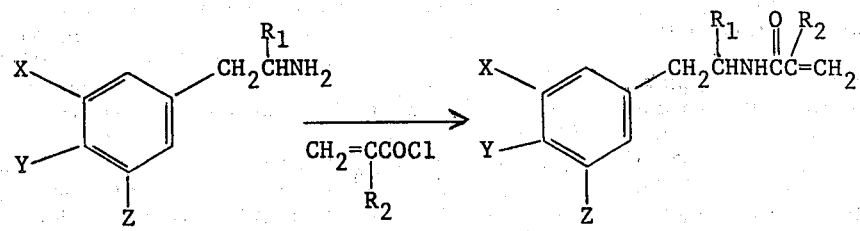

Compound No. 1 in which
X is an alkoxy group of one to four carbon atoms,
Y is an alkoxy group of one to four carbon atoms or X taken with Y is a methylenedioxy group (—O—CH$_2$—O—),
Z is hydrogen or an alkoxy group of one to four carbon atoms, and $R_1$ and $R_2$ each is hydrogen or an alkyl group of one to four carbon atoms.

The above reaction may be identified as Step No. 1 and the resulting compound may be called Compound No. 1.

Then Compound No. 1 may be further reacted by heating it at an elevated temperature, suitably about 80° C, with a secondary amine in an organic solvent such as benzene or ethyl alcohol. This reaction may be written as follows:

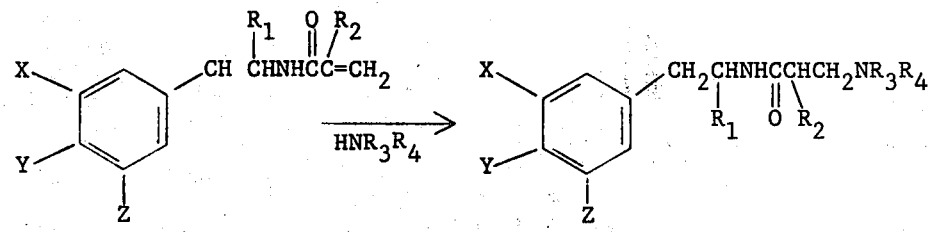

Compound No. 1                Compound No. 2 in which X, Y, Z, $R_1$ and $R_2$ are the same as designated in connection with Step No. 1 and $R_3$ and $R_4$ each is an alkyl group of one to four carbon atoms or $R_3$ taken with $R_4$ and N is pyrrolidinyl, piperidino, morpholino, or 1,2,3,4-tetrahydroisoquinolyl. This reaction may be called Step No. 2 and the resulting compound may be called Compound No. 2.

Alternately, and instead of Steps No. 1 and No. 2 above described, the phenethylamine is reacted with 2-chloroalkanoyl chloride in the presence of an acid acceptor such as triethylamine in an inert solvent such as benzene. This reaction may be written:

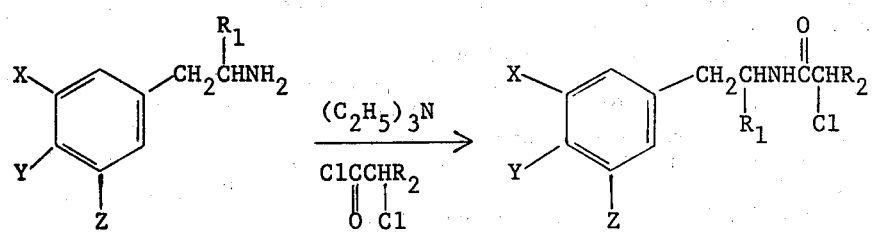

Compound No. 1a where X, Y, Z, and $R_1$ are the same as designated in connection with Step No. 1.

This reaction may be called Step No. 1a and the resulting compound may be called Compound No. 1a.

Then Compound No. 1a may be further reacted with a secondary amine in an inert solvent such as benzene. This reaction may be written:

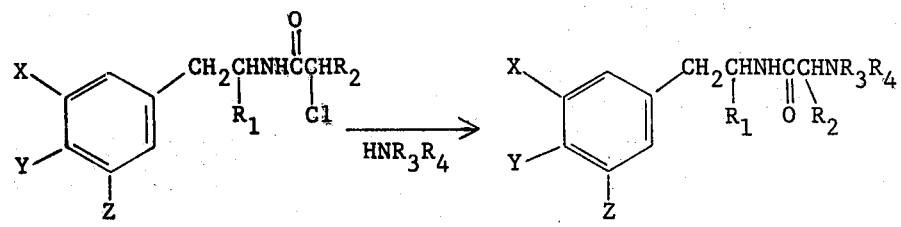

Compound No. 1a                Compound No. 2a where X, Y, Z, $R_1$, $R_2$, $R_3$ and $R_4$ are the same as designated in Step No. 2, and the resulting compound may be called Compound No. 2a.

Compound No. 2 or 2a may be cyclized and this may be done using phosphorous oxychloride in chloroform at a temperature of about 25° C or phosphorous pentachloride in chloroform at a temperature of about 65° C. This reaction may be written:

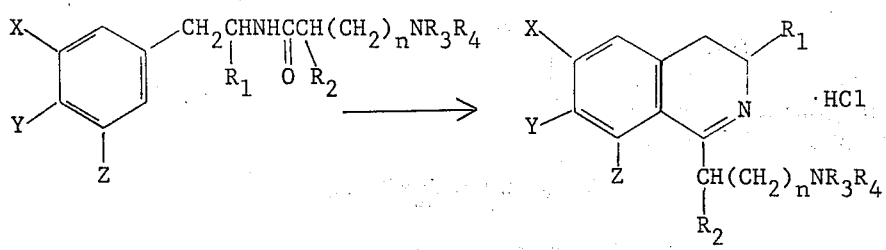

Compound No. 2 and 2a → Compound No. 3 where X, Y, Z, $R_1$, $R_2$, $R_3$ and $R_4$ are designated as in Compound No. 2 or 2a and $n$ is one or zero. This reaction may be called Step No. 3 and the resulting compound may be called Compound No. 3.

Compound No. 3 may be hydrogenated in aqueous ethyl alcohol solution at a pressure of 2 or 3 atmospheres in the presence of a platinum catalyst. This reaction may be written:

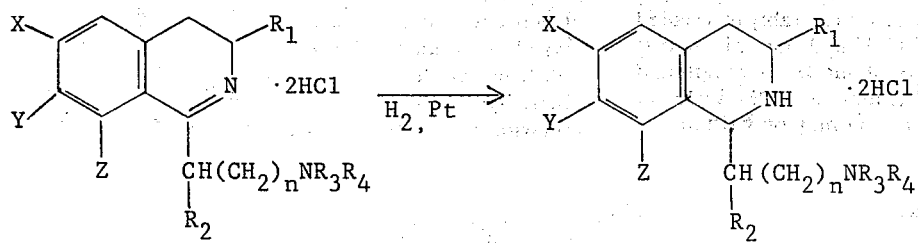

Compound No. 3 → Compound No. 4 where X, Y, Z, $R_1$, $R_2$, $R_3$ and $R_4$ are as designated in Compound No. 2 and $n$ is one or zero. This reaction may be called Step No. 4 and the resulting compound may be called Compound No. 4.

We may prepare compounds which are represented in the above structure for Compound No. 4 where $R_2$ is alkyl of one to four carbon atoms, phenyl, pyrrolidinomethyl, piperidinomethyl, morpholinomethyl, by starting with an alpha-amino alkylation. To prepare these compounds an 1-n-alkylisoquinoline compound or a 1-benzylisoquinoline compound is reacted with formaldehyde and a secondary amine in a lower aliphatic alcohol at reflux temperature. In the case where $R_2$ in Compound No. 4 above is equal to an alkyl group of one to four carbon atoms or a phenyl group and where n equals one, the α-amino alkylation reaction may be written starting with a Compound No. 6 to give a Compound No. 3a as follows:

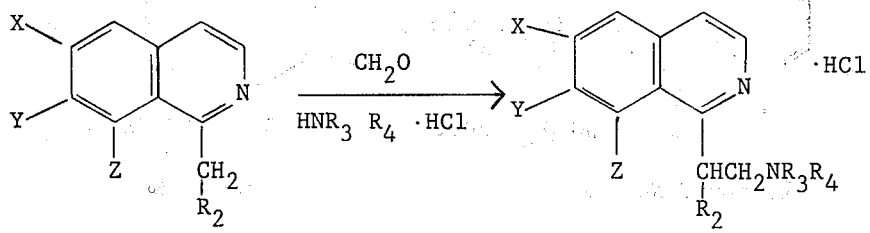

Compound No. 6 → Compound No. 3a wherein X, Y, Z, $R_3$ and $R_4$ are the same as defined in Compound No. 2 and $R_2$ is an alkyl group of one to four carbon atoms or a phenyl group.

Compound No. 3a may be hydrogenated in aqueous ethyl alcohol in the presence of a platinum catalyst at about 2 or 3 atmospheres pressure to yield the dihydrochloride. The reaction may be written as follows:

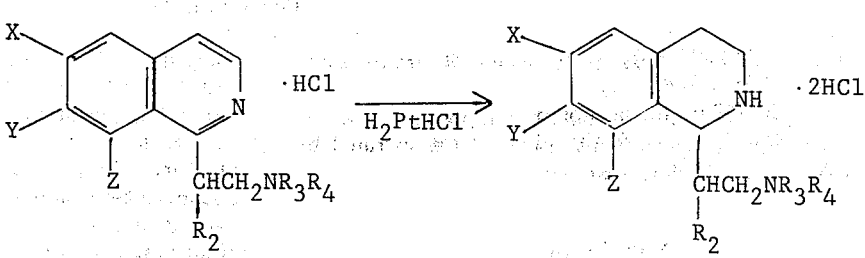

Compound No. 3a → Compound No. 4a wherein X, Y, Z, $R_2$, $R_3$ and $R_4$ are the same as in the above reaction to produce Compound No. 3a.

In the case where $R_2$ in Compound No. 4 is pyrrolidinomethyl, piperidinomethyl, morpholinomethyl and n equals one, the α-amino alkylation reaction may be performed using a 1-methylisoquinoline compound wherein X, Y, Z, $R_3$ and $R_4$ are as defined above for Compound No. 2. The reaction may be written as follows to produce Compound No. 3b:

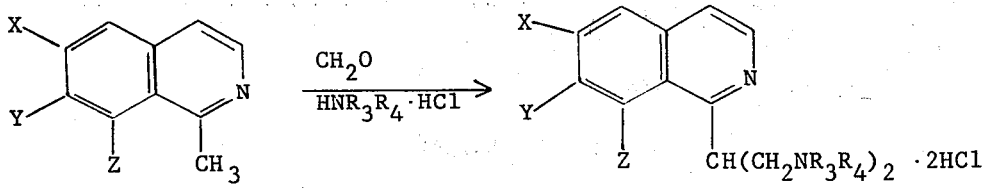

Compound No. 3b

Compound No. 3b may be hydrogenated in aqueous ethyl alcohol in the presence of a platinum catalyst at about 2 or 3 atmospheres pressure to yield the dihydrochloride. The reaction may be written as follows:

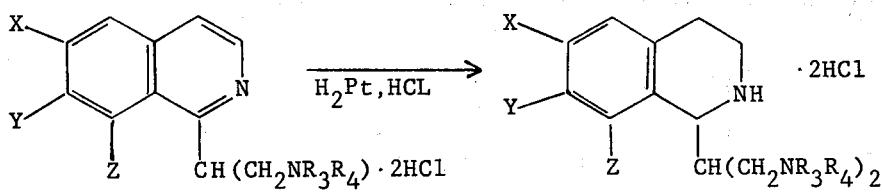

Compound No. 3b      Compound No. 4b wherein X, Y, Z, $R_3$ and $R_4$ are the same as defined in Compound No. 2.

Compounds No. 4, 4a or 4b may be reacted to convert X and Y of such compound to hydroxy groups, and if alkoxy groups are contained in Z, to convert such alkoxy groups to hydroxy groups, by refluxing hydrobromic acid, or hydrochloric acid preferably in a sealed tube, at about 140° to 160° C. If hydrobromic acid is used it may be of the order of about 48% strength and if hydrochloric acid is used it may be of the order of about 38% strength. This reaction may be written:

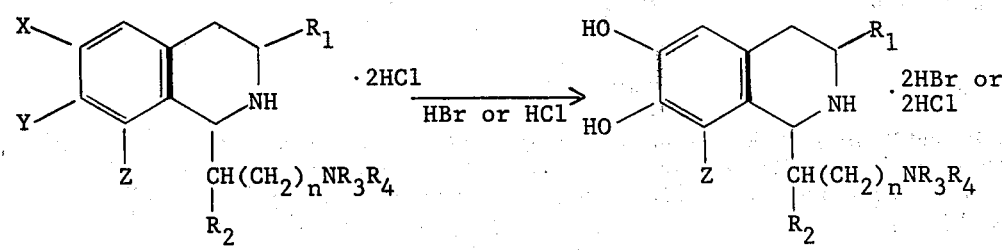

Compound No. 5

In Compound No. 5, Z, $R_1$, $R_2$, $R_3$ and $R_4$ are the same as in the general formula.

The preparation of particular compounds in accordance with our invention is further demonstrated by the following specific examples:

EXAMPLE I 6,7-Dihydroxy-1-(2-morpholinoethyl)-1,2,3,4-tetrahydroisoquinoline dihydrobromide (P-3374)

Step 1. To a well-stirred solution of 0.5 mole of 3,4-dimethoxyphenethyl amine in 400 ml of dry benzene was added dropwise, under a nitrogen atmosphere, a solution of 0.5 mole of acryloyl chloride in 400 ml of dry benzene. During the addition, the temperature of the reaction mixture was maintained at 5°–10° C by means of an external ice-salt bath. This was followed by the slow addition of 263 ml of a 2N sodium hydroxide solution at approximately 10° C. The reaction mixture was stirred one hour at 25° C, the organic layer separated, washed with water and dried. Removal of the benzene in vacuum left a thick, slightly yellow oil whose infrared spectrum was consistent with the assigned structure of N-acryloyl-3,4-dimethoxyphenethylamine.

Step 2. The amide from Step 1, in 400 ml of dry benzene was condensed with 0.67 mole of morpholine under reflux for three hours. The solvent was removed in vacuum and the residue crystallized from a mixture of benzene and cyclohexane to give 127 g of a white crystalline product, M.P. 87° to 89° C. This was identified from its elemental analysis as N-(3,4-dimethoxyphenethyl)-3-morpholinopropionamide. The infrared spectrum was consistent with its assigned structure.

Analysis — Calculated for $C_{17}H_{26}N_2O_4$: C, 63.33; H, 8.13; N, 8.69. Found: C, 62.23; H, 8.10; N, 8.66.

Step 3. Cyclization of the amide obtained in Step 2 was effected by dissolving 0.2 mole of this amide in 200 ml of dry chloroform and adding this solution, portionwise, to a suspension of 0.4 mole of phosphorous pentachloride in 200 ml of dry chloroform. The reaction mixture was allowed to stand at 25° C while protected with a calcium chloride drying tube, for 24 hours, then concentrated in vacuum to a red oil. This oil was treated cautiously with, then dissolved in, 150 ml of isopropyl alcohol and allowed to cool. From the solution was collected 62 g of a light yellow solid, M.P. 139° to 140° C (from ethyl alcohol) which analyzed as the hemihydrate, 3,4-dihydro-6,7-dimethoxy-1-(2-morpholinoethyl) isoquinoline dihydrochloride hemihydrate. A similar cyclization, using phosphorous oxychloride in chloroform under reflux for three hours gave the same product. The infrared spectrum was consistent with the assigned structure.

Analysis — Calculated for $C_{34}H_{54}Cl_4N_4O_7$: C, 52.86; H, 7.05; N, 7.26. Found: C, 52.70; H, 7.15; N, 6.91.

Step 4. Hydrogenation of a solution of 0.055 mole of the dihydroisoquinoline from Step 3 in 250 ml of 80% aqueous ethyl alcohol over 0.2 gm platinum oxide catalyst and at 2.5 atmospheres of hydrogen gave a rapid and quantitative uptake of hydrogen. After filtration, the filtrate was concentrated in vacuum to an oil which was crystallized from ethyl alcohol to give 17.5 gm of a white crystalline product, M.P. 250° to 252° C (dec.) which analyzed as 6,7-dimethoxy-1-(2-morpholinoethyl)-1,2,3,4-tetrahydroisoquinoline dihydrochloride monohydrate. The infrared spectrum was consistent with the assigned structure.

Analysis — Calculated for $C_{17}H_{30}Cl_2N_2O_4$: C, 51,39; H, 7.61; N, 7.05. Found: C, 51.76; H, 7.32; N, 6.93.

Step 5. The dimethoxyisoquinoline obtained in Step 4 was demethylated by heating a solution of 0.32 mole of the compound in 800 ml of 48% aqueous hydrobromic acid under reflux for three hours. After cooling the reaction mixture at 0° C for 16 hours, it was filtered to give 128 gm of a white crystalline product, M.P. 283° to 284° C (dec.).

Recrystallization from aqueous methyl alcohol did not change the melting point. The infrared spectrum was consistent for the title compound, 6,7-dihydroxy-1-(2-morpholinoethyl)- 1,2,3,4-tetrahydroisoquinoline dihydrobromide.

Analysis — Calculated for $C_{15}H_{24}Br_2N_2O_3$: C, 40.92; H, 5.49; N, 6.37. Found: C, 41.13; H, 5.55; N, 6.40.

EXAMPLE II 6,7-Dihydroxy-1-(2-piperidinoethyl)-1,2,3,4-tetrahydroisoquinoline dihydrobromide (P-3321)

By replacing the morpholine used in Example I, Step 2, with an equivalent of piperidine and carrying out the subsequent set of reactions as in Example I, Steps 2, 3, 4 and 5, there was obtained a white, crystalline material which melted 262° to 263° C (dec.) (from methyl alcohol), whose infrared spectrum was consistent with the assigned structure.

Analysis — Calculated for $C_{16}H_{26}Br_2N_2O_2$: C, 43.85; H, 5.98; N, 6.39. Found: C, 43.97; H, 6.00; N, 6.19.

EXAMPLE III 1-(2-Diethylamineoethyl)-6,7-dihydroxy-1,2,3,4-tetrahydroisoquinoline dihydrobromide (P-3386)

Replacing the morpholine used in Example I, Step 2 with an equivalent of diethyl amine and carrying out the subsequent set of reactions as in Example I, Steps 2, 3, 4 and 5 gave the product as a white, crystalline solid, M.P. 224° to 226° C (dec.) from ethyl alcohol. The infrared spectrum was consistent with the assigned structure.

Analysis — Calculated for $C_{15}H_{26}Br_2N_2O_2$: C, 42.27; H, 6.15; N, 6.57. Found: C, 42.17; H, 6.13; N, 6.30.

EXAMPLE IV 6,7-Dihydroxy-1[2-[1-(4-methyl)piperazinyl]ethyl]-1,2,3,4-tetrahydroisoquinoline trihydrobromide (P-3408)

Replacing the morpholine used in Example I, Step 2, with an equivalent of N-methylpiperazine and carrying out the subsequent set of reactions as in Example I, Steps 2, 3, 4 and 5 gave the product as a white crystalline solid, M.P. 260° to 262° C (dec.) (from aqueous methyl alcohol). The infrared spectrum agreed with the assigned structure.

Analysis — Calculated for $C_{16}H_{28}Br_{3}N_3O_2$: C, 35.98; H, 5.29; N, 7.87. Found: C, 35.90; H, 5.34; N, 7.66.

EXAMPLE V 6,7-Dihydroxy-1-[2-[2-(1,2,3,4-tetrahydro)isoquinolyl[ethyl[-1,2,3,4-tetrahydroisoquinoline dihydrobromide hemihydrate (P-3445)

Replacing the morpholine used in Example I, Step 2, with an equivalent of 1,2,3,4-tetrahydroisoquinoline and carrying out the set of reactions as in Example I, Steps 2, 3, 4 and 5 gave a non-crystalline, resin-like material which could not be crystallized. The infrared spectrum agreed with the assigned structure.

Analysis — Calculated for $C_{40}H_{54}Br_4N_4O_5$: C, 48.51; H, 5.50; N, 5.66. Found: C, 48.62; H, 5.63; N, 5.39.

EXAMPLE VI 6,7-Methylenedioxy-1-(2-morpholinoethyl)-1,2,3,4-tetrahydroisoquinoline dihydrochloride (P-3516)

Replacing the 3,4-dimethoxyphenethylamine used in Example I, Step 1 with an equivalent of 3,4-methylenedioxyphenethylamine and carrying out the set of reactions as in Example I, Steps 1, 2, 3 and 4 gave the product as a white solid with ethyl alcohol, M.P. 259° C (dec.). The infrared spectrum agreed with the assigned structure.

Analysis — Calculated for $C_{16}H_{24}Cl_2N_2O_3$: C, 52.90; H, 6.66; N, 7.71. Found: C, 52.95; H, 6.66; N, 7.22.

EXAMPLE VII 6,7-Dihydroxy-3-methyl-1-(2-morpholinoethyl)-1,2,3,4-tetrahydroisoquinoline dihydrobromide (P-3433)

Replacing the 3,4-dimethoxyphenethylamine used in Example I, Step 1 with an equivalent of 1-(3,4-dimethoxyphenyl)-2-propylamine and carrying out the subsequent reactions as in Example I, Steps 1, 2, 3, 4 and 5 gave the product as a white, crystalline solid from aqueous ethyl alcohol, M.P. 286° C (dec.). The infrared spectrum agreed with the assigned structure.

Analysis — Calculated for $C_{16}H_{26}Br_2N_2O_3$: C, 42.31; H, 5,77; N, 6.17. Found: C, 42.45; H, 5.80; N, 5.99.

EXAMPLE VIII 1-(2-Morpholinoethyl)-1,2,3,4-tetrahydro-6,7,8-trihydroxyisoquinoline dihydrobromide (P-3494)

Replacing the 3,4-dimethoxyphenethylamine used in Example I, Step 1 with an equivalent of 3,4,5-trimethoxyphenethylamine and carrying out the subsequent reactions as in Example I, Steps 1, 2, 3, 4 and 5 gave the product as a slightly tan solid from aqueous methanol M.P. 266° C (dec.). The infrared spectrum agreed with the assigned structure.

Analysis — Calculated for $C_{15}H_{24}Br_2N_2O_4$: C, 39.48; H, 5.30; N, 6.14. Found: C, 39.22; H, 5.42; N, 5.77.

EXAMPLE IX 6,7-Dihydroxy-1-morpholinomethyl-1,2,3,4-tetrahydroisoquinoline dihydrobromide (P-3514)

A solution of 0.25 mole of chloroacetyl chloride in 75 ml of dry benzene was added dropwise, at 0° C to a stirred solution of 0.26 mole triethylamine and 0.3 mole of 3,4-dimethoxyphenethylamine in 350 ml of dry benzene. The reaction mixture was stirred two hours at 25° C, warmed to approximately 50° C, filtered, then the benzene solution treated with 0.5 mole of morpholine at reflux for 5 hours. From this was isolated 58 g of product, isolated as the oxalate from ethyl alcohol, N-(3,4-dimethoxyphenethyl)--2-morpholinoacetamide oxalate, M.P. 226° to 228° C. The infrared spectrum and elemental analysis agreed with the assigned structure. This material was treated as in Example I, Steps 3, 4 and 5 to give the title compound, M.P. 278° C (dec.), from aqueous methyl alcohol. The infrared spectrum was consistent with the assigned structure.

Analysis — Calculated for $C_{14}H_{22}Br_2N_2O_3$: C, 39.46; H, 5.21; N, 6.57. Found: C, 39.21; H, 5.45; N, 6.32.

EXAMPLE X 6,7-Dihydroxy-1-[2-morpholino)propyl]-1,2,3,4-tetrahydroisoquinoline dihydrobromide (P-3479)

A mixture of 0.064 mole of 6,7-dimethoxy-1-ethylisoquinoline, 0.1 mole morpholine, 0.11 mole of paraformaldehyde and 0.1 mole of concentrated hydrochloric acid was heated under reflux for 3 hours, 0.07 mole of additional paraformaldehyde was added and refluxing continued another 2 hours. The reaction mixture was concentrated in vacuum to an oil which was crystallized from a mixture of ethyl alcohol and methyl alcohol to give 9.8 g of solid, M.P. 216° to 217° C (dec.) which from its infrared spectrum was assigned the structure, 6,7-dimethoxy-1-[2-(1-morpholino) propyl] isoquinoline dihydrochloride. This material in 125 ml of 80% aqueous ethyl alcohol was hydrogenated over 0.2 g platinum oxide and 2.5 atmospheres of hydrogen for 14 hours. Then the gum was isolated and treated with 48% aqueous hydrobromic acid as in Example I, Step 5, to give the title product, M.P. 260° to 261° C (dec.) from aqueous isopropyl alcohol. The infrared spectrum was consistent with the assigned structure.

Analysis — Calculated for $C_{16}H_{26}Br_2N_2O_3$: C, 42.31; H, 5.77; N, 6.17. Found: C, 42.13; H, 5.72; N, 5.93.

EXAMPLE XI

1-[2-(1,3-Bismorpholino)propyl]-6,7-dihydroxy-1,2,3,4-tetrahydroisoquinoline trihydrobromide (P-3477)

A mixture of 0.088 mole of 6,7-dimethoxy-1-methylisoquinoline, 0.2 mole of morpholine, 0.21 mole of paraformaldehyde and 0.2 mole of concentrated hydrochloric acid was heated under reflux for 2 hours, then an additional 0.1 mole of morpholine and 0.1 mole of paraformaldehyde was added and the mixture heated under reflux another 2 hours. The reaction mixture was concentrated in vacuum to a red oil which was chromatographed on Silica Gel with ethyl alcohol to give 12 g of a solid, M.P. 129° to 131° C (from cyclohexane) which from its infrared spectrum and elemental analysis was identified as 1-[2-(1,3-bismorpholino)-propyl]-6,7-dimethoxyisoquinoline.

Analysis — Calculated for $C_{22}H_{31}N_3O_4$: C, 65.81; H, 7.78; N, 10.46; Found: C, 65.63; H, 7.76; N, 10.20.

This material in 110 ml of 90% aqueous ethyl alcohol was treated with concentrated hydrochloric acid until the solution was slightly acid, then 0.2 g of platinum oxide was added and the mixture placed under 2.5 atmospheres of hydrogen. Absorption was slow, the theoretical amount of hydrogen being absorbed in ten hours. The solution was filtered, the filtrate concentrated in vacuum to an oil, then this oil, which solidified but appeared to be hydroscopic, was treated with 48% aqueous hydrobromic acid as in Example I, Step 5 to give a white crystalline product from 98% aqueous methyl alcohol, M.P. 248° to 250° C (dec.). The infrared spectrum was consistent with the assigned structure.

Analysis — Calculated for $C_{20}H_{34}Br_3N_3O_4$: C, 38.73; H, 5.52; N, 6.78. Found: C, 38.65; H, 5.67; N, 6.52.

EXAMPLE XII 6,7-Dihydroxy-1-[α-(morpholinomethyl)benzyl]-1,2,3,4-tetrahydroisoquinoline dihydrobromide (P-3478)

A solution of 0.079 mole of 1-benzyl-6,7-dimethoxyisoquinoline, 0.12 mole morpholine, 0.13 mole of paraformaldehyde and 0.41 mole of concentrated hydrochloric acid in 175 ml of ethyl alcohol heated under reflux 6 hours gave 15 g of a white solid, M.P. 125° to 126° C (from cyclohexane-hexane). This material, in 250 ml of 50% aqueous ethyl alcohol was treated with 0.2 g of platinum oxide and placed under 2.5 atmospheres of hydrogen. The theoretical amount of hydrogen was absorbed in 10 hours. After filtration, the filtrate was concentrated in vacuum to an oil which was crystallized from aqueous isopropyl alcohol to give 9.5 g of 6,7 dimethoxy-1-(α-(morpholinomethyl)benzyl) 1,2,3,4-tetrahydroisoquinoline dihydrochloride, M.P. 208° C (dec.). The infrared spectrum was consistent with the assigned structure.

Analysis — Calculated for $C_{23}H_{32}Cl_2N_2O_3$: C, 60.66; H, 7.08; N, 6.15. Found: C, 61.10; H, 6.34; N, 5.96;

This material was heated under reflux with 48% aqueous hydrobromic acid as in Example I, Step 5 to give a white crystalline solid from 95% aqueous ethyl alcohol, M.P. 244° to 245° C. The infrared spectrum was consistent with the assigned structure.

Analysis — Calculated for $C_{21}H_{28}Br_2N_2O_3$: C, 48.85; H, 5.47; N, 5.43. Found: C, 48.82; H, 5.57; N, 5.14.

The specific compounds obtained in Examples I to XII were tested in nembutal anesthetized dogs to measure their effectiveness for reducing vascular resistance at different dosage levels. Blood flow measurements were taken in the carotid and femoral arteries at the time of maximal flow increases occurring one minute or more after intravenous administration of a test compound. The data so obtained is given in Table No. 1. The numerical values given in this table represent percent decrease in vascular resistance, and the vascular resistance is determined by dividing blood pressure by blood flow.

TABLE I

COMPARISON OF ACTIVITY WITH STANDARD DRUGS

| | Percent Decrease in Vascular Resistance | | | | | | | |
|---|---|---|---|---|---|---|---|---|
| | Carotid Vasculature | | | | Femoral Vasculature | | | |
| Compound | 1 | Dose γ/Kg 10 | 100 | 1000 | 1 | Dose γ/Kg 10 | 100 | 1000 |
| Isoxsuprine | 6 | 25 | 45 | 59 | 8 | 15 | 26 | 61 |
| Nylidrin | 19 | 27 | 37 | 55 | 14 | 35 | 41 | 45 |
| P-3321 | 9 | 34 | 74 | 81 | 4 | 23 | 61 | 69 |
| P-3374 | 31 | 70 | 81 | 83 | 16 | 67 | 79 | 71 |
| P-3408 | 0 | 0 | 12 | 40 | 0 | 0 | 7 | 39 |
| P-3433 | 0 | 0 | 11 | 19 | 0 | 0 | 3 | 0 |
| P-3445 | 16 | 38 | 54 | 64 | 0 | 0 | 36 | 64 |
| P-3477 | 0 | 0 | 23 | 51 | 0 | 0 | 15 | 56 |
| P-3478 | 0 | 0 | −13 | −11 | 0 | 0 | 0 | 30 |
| P-3479 | 18 | 44 | 45 | 36 | 18 | 19 | 24 | 26 |
| P-3494 | 6 | 60 | 74 | 78 | 0 | 0 | 29 | 52 |
| P-3514 | 34 | 53 | 77 | 58 | 18 | 58 | 80 | 66 |
| P-3516 | 0 | 0 | 23 | 65 | 0 | 45 | 42 | 37 |

TABLE I-continued

COMPARISON OF ACTIVITY WITH STANDARD DRUGS

| Compound | Percent Decrease in Vascular Resistance | | | | | | | |
|---|---|---|---|---|---|---|---|---|
| | Carotid Vasculature | | | | Femoral Vasculature | | | |
| | Dose γ/Kg | | | | Dose γ/Kg | | | |
| | 1 | 10 | 100 | 1000 | 1 | 10 | 100 | 1000 |
| P-3386 | 0 | 5 | 27 | 97 | 0 | 0 | 5 | −11 |

In Table I, each of the compounds tested was shown to be effective in reducing vascular resistance. This data also shows variation in the dosage level for effectiveness with respect to each of the drugs tested.

While only certain embodiments of our invention have been described and demonstrated in detail, it is understood that the invention may take many and various forms and is subject to wide variation all within the spirit of the invention and the scope of the following claims.

We claim:

1. A compound having the structure:

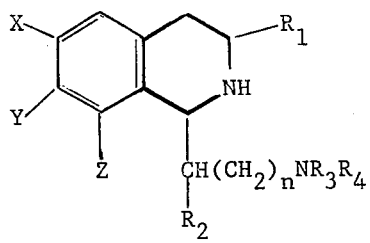

wherein
X is a hydroxy group and
Y is a hydroxy group, or
X taken with Y is a methylenedioxy group (—O—CH$_2$—O—)
Z is hydrogen or a hydroxy group
$R_1$ is hydrogen or an alkyl group of one to four carbon atoms,
$R_2$ is hydrogen, an alkyl group of one to four carbon atoms, phenyl, pyrrolidinomethyl, piperidinomethyl, or morpholinomethyl,
$R_3$ and $R_4$ each is an alkyl group of one to four carbon atoms or $R_3$ taken with $R_4$ and N is pyrrolidinyl piperidino, morpholino, or 2-(1,2,3,4-tetrahydroisoquinolyl), and
$n$ is one or zero.

2. A compound as set forth in claim 1 in which $n$ is one.

3. A compound as set forth in claim 1 in which $n$ is zero.

4. A compound as set forth in claim 1 in which X and Y each is a hydroxy group.

5. A compound as set forth in claim 1 in which X taken with Y is —O—CH$_2$—O—.

6. A compound as set forth in claim 1 in which
X and Y each is hydroxy,
Z, $R_1$ and $R_2$ each is hydrogen,
$R_3$ and $R_4$ taken with N is morpholino, and
$n$ is one.

7. A compound as set forth in claim 1 in which
X and Y each is hydroxy,
Z, $R_1$ and $R_2$ each is hydrogen,
$R_3$ and $R_4$ taken with N is 2-(1,2,3,4-tetrahydroisoquinolyl), and
$n$ is one.

8. A compound as set forth in claim 1 in which
X and Y each is hydroxy,
Z and $R_1$ each is hydrogen,
$R_2$ is methyl,
$R_3$ and $R_4$ taken with N is morpholino, and
$n$ is one.

9. A compound as set forth in claim 1 in which
X and Y each is hydroxy,
Z, $R_1$ and $R_2$ each is hydrogen,
$R_3$ and $R_4$ taken with N is piperidino, and
$n$ is one.

10. A compound as set forth in claim 1 in which
X, Y and Z each is hydroxy,
$R_1$ and $R_2$ each is hydrogen,
$R_3$ and $R_4$ taken with N is morpholino, and $n$ is one.

11. A compound as set forth in claim 1 in which
X and Y each is hydroxy,
Z, $R_1$ and $R_2$ each is hydrogen,
$R_3$ and $R_4$ taken with N is morpholino, and
$n$ is zero.

12. A compound as set forth in claim 1 in which
X taken with Y is -O-CH$_2$-O-,
Z, $R_1$ and $R_2$ each is hydrogen,
$R_3$ and $R_4$ taken with N is morpholino, and
$n$ is one.

13. A pharmaceutically acceptable acid addition salt of the compounds set forth in claim 1.

* * * * *